(12) United States Patent
Berzak et al.

(10) Patent No.: US 8,906,004 B2
(45) Date of Patent: Dec. 9, 2014

(54) PHASE SEPARATION OF CRYOGEN IN CRYOSURGICAL INSTRUMENT

(71) Applicant: Icecure Medical Ltd., Caesarea (IL)

(72) Inventors: Nir Berzak, Tel Aviv (IL); Ron Hilleli, Zichron Yaacov (IL)

(73) Assignee: Icecure Medical Ltd., Caesarea (IL)

( * ) Notice: Subject to any disclaimer, the term of this patent is extended or adjusted under 35 U.S.C. 154(b) by 0 days.

(21) Appl. No.: 14/204,175

(22) Filed: Mar. 11, 2014

(65) Prior Publication Data

US 2014/0194863 A1 Jul. 10, 2014

Related U.S. Application Data

(63) Continuation-in-part of application No. 13/232,203, filed on Sep. 14, 2011, now Pat. No. 8,709,005.

(60) Provisional application No. 61/484,822, filed on May 11, 2011.

(51) Int. Cl.
*A61B 18/02* (2006.01)

(52) U.S. Cl.
CPC .............. *A61B 18/02* (2013.01); *A61B 18/0218* (2013.01); *A61B 2018/0287* (2013.01)
USPC .......................................................... 606/23

(58) Field of Classification Search
CPC ...................................................... A61B 18/02
USPC .................................................... 606/20–26
See application file for complete search history.

(56) References Cited

U.S. PATENT DOCUMENTS

| | | | |
|---|---|---|---|
| 3,696,813 A * | 10/1972 | Wallach | 606/26 |
| 3,800,552 A | 4/1974 | Sollami et al. | |
| 5,522,870 A | 6/1996 | Ben-Zion | |
| 5,800,487 A | 9/1998 | Mikus et al. | |
| 6,706,037 B2 | 3/2004 | Zvuloni et al. | |

(Continued)

FOREIGN PATENT DOCUMENTS

WO 2009/128014 A1 10/2009

OTHER PUBLICATIONS

International Search Report and Written Opinion of the International Searching Authority in co-pending International Application No. PCT/US2011/051529.

*Primary Examiner* — Michael Peffley
*Assistant Examiner* — Daniel Fowler
(74) *Attorney, Agent, or Firm* — The Law Office of Michael E. Kondoudis

(57) ABSTRACT

A cryosurgical instrument including: a shaft having a closed distal end defining an expansion chamber and an open proximal end that receives an inflow of cryogen and to exhaust a flow of expanded cryogen; and a heat exchanger with a cryogen delivery tube that spirals around a core disposed along longitudinal axis thereof. The cryogen delivery tube, at least where it spirals, is in fluid tight contact with the inner surface of the shaft so as to form spiraling cryogen exhaust pathways that extend along a portion of a length of the cryosurgical instrument from the distal end of the shaft. The cryogen delivery tube forces a two-phase flow of cryogen to undergo phase separation by centrifugal forces and urges the liquid phase against the external walls of the spiral coil and the outer surface of the spiral gap. Heat exchanging, through boiling, occurs close to the external wall of the instrument.

6 Claims, 2 Drawing Sheets

(56) References Cited

U.S. PATENT DOCUMENTS

| | | |
|---|---|---|
| 2005/0043725 A1 | 2/2005 | Duong et al. |
| 2006/0079867 A1 | 4/2006 | Berzak et al. |
| 2006/0253114 A1* | 11/2006 | Saadat .......................... 606/21 |
| 2007/0149957 A1 | 6/2007 | Ross et al. |
| 2007/0149959 A1 | 6/2007 | DeLonzor et al. |
| 2009/0163902 A1 | 6/2009 | DeLonzor et al. |
| 2009/0182320 A1 | 7/2009 | DeLonzor et al. |

* cited by examiner

PHASE SEPARATION OF CRYOGEN IN CRYOSURGICAL INSTRUMENT

CROSS-REFERENCE TO RELATED APPLICATIONS

This application is a continuation in part of U.S. patent application Ser. No. 13/232,203, which was filed on Sep. 14, 2011 and is now U.S. Pat. No. 8,709,005. Also, this application claims the benefit of U.S. Provisional Patent Application No. 61/484,822, which was on filed May 11, 2011. The disclosures of both of these applications are incorporated by reference in their entireties.

BACKGROUND

1. Technical Field

Embodiments of the present invention relate generally to cryosurgical instruments such as cryoprobes and, more particularly, to phase separation of cryogen in cryosurgical instruments for heat exchanging advantage.

2. Description of related art

It is known to employ coiled heat exchangers in cryosurgical instruments with cryogen supplied as a pressurized gas. In such heat exchangers, the expansion of the gas causes it to change its temperature. As explained in U.S. Pat. No. 6,706,037, for example, this phenomenon is referred to as the "Joule-Thomson effect", thermodynamically known as adiabatic expansion.

It is also known, in coiled heat exchangers, to use gases that cool upon expansion, such as Argon or Nitrogen, for cooling, and gases that heat as a result of the expansion, such as Helium, for heating. In these heat exchangers, the return gases are commonly used to recycle the thermal energy (i.e., the return cooling gas not only cools the outer surface of the cryosurgical instrument but also the inlet pressurized gas). The coil shape increases the contact area between cool fluids to hot fluids. The heat transfer between these fluids is proportional to the contact surface between them. Thus, the coil serves as an advantageous solution for such heat regeneration. See, for example, U.S. Pat. No. 6,706,037 (at column 15 lines 40-58, and column 16 lines 65-68). Also, as discussed in U.S. Pat. Nos. 3,800,552 and 5,522,870, lowering the inlet temperature may liquefy the expanded gas.

Still further, approaches to enhancing the cooling and heating regeneration are known. For example, U.S. Pat. No. 5,800,487 discusses enhancing the cooling and heating regeneration by supplying the inlet pressurized gas tube with fins to increase the area of the heat exchanging.

If the cryogen is supplied as a liquid or a two-phase (gas/liquid) fluid, cooling methods use the energy required for the change of phase of the inlet cryogen. In this case, the temperature of the inlet fluid and the return fluid may be the same or close in value, and would minimize, or annul heat exchange between the inlet and outlet fluids, due to a small differential temperature. The application of a coil serves as a separator of the phases in a two-phase flow. This is because the liquid phase has greater specific gravity, which tends to cause the liquid phase toward the outer (greater) diameter. The greater diameter of the coil is close to the external surface and, as a result, the boiling or change of phase of the liquid occurs close to the external surface. This arrangement utilizes the physical shape of the coil as a centrifugal force generator to separate the heavier liquid phase from the lighter gaseous phase, forcing (urging) the liquid towards the outer surface of the coil.

When the cryogens, either in gaseous form or two-phase form, enter in a straight inlet tube, or lumen, flow directing elements (such as those described in U.S. Pat. No. 5,800,487) or baffles (such as those described in U.S. Patent Publication No. 2009/0163902 A1, U.S. Patent Publication No. 2007/0149957 A1, U.S. Patent Publication No. 2007/0149959 A1, and U.S. Patent Publication No. 2009/0182320 A1) have been used.

BRIEF SUMMARY

In one aspect, the inventors have discovered a new and novel strategy that yields increased performance of a cryosurgical device by selectively locating the boiling of cryogen in the device. In one exemplary implementation, a cryosurgical instrument includes a coiled tube that serves as both a cryogen delivery tube and a phase separator that separates cryogen into liquid and gaseous phases. A fluid cryogen flows into the coiled tube that, in turn, is in energy exchange contact with the outer wall of a portion of a cryosurgical instrument. The incoming flow spins as it spirals such that it separates into the two phases, with the heaver liquid phase being urged (i.e., forced) into contact with the outer wall of the coil, which is in contact with the outer wall of the cooling zone. This increases the heat exchanging, by boiling, with the outer wall of the cryosurgical instrument. In the return flow passage, between the coil and the cylindrical outer surface of the cryosurgical device, the same centrifugal force separate the liquid from the gaseous phase, forcing the liquid towards the outer surface of the external wall of the cryosurgical instrument by centrifugal force. The heat exchange zone comprises at least the distal/downstream tip of the cryosurgical instrument, from the tip of the probe to the insulation, where the fluid is in contact with the outer shaft's inner surface. In this way, the centrifugal force can be advantageously used.

According to another aspect of the present invention, there is provided a cryosurgical instrument including: a shaft having a closed distal end defining an expansion chamber and an open proximal end adapted and configured (i) to receive an inflow of cryogen and (ii) to exhaust a flow of expanded cryogen; and a heat exchanger. The heat exchanger includes: a solid core element extending along a longitudinal axis of the heat exchanger; and a cryogen delivery tube that spirals around and contacts the solid core element. The spirals of the cryogen delivery tube are spaced from each other and in fluid tight contact with the solid core and an inner surface of the shaft so as to form a spiraling cryogen exhaust pathway from the distal end of the shaft to the proximal end of the shaft.

According to another aspect of the present invention, there is provided a cryosurgical instrument including: a shaft having a closed distal end defining an expansion chamber at which cryogen boils and a proximal end adapted and configured (i) to receive an inflow of cryogen, (ii) deliver the inflow of cryogen to the expansion chamber, and (iii) to exhaust a flow of cryogen that has expanded in the expansion chamber; a solid core element extending along a longitudinal axis of the shaft; and a helical cryogen delivery tube that spirals around the core, is in fluid tight contact with the core, and is in fluid tight contact with an inner surface of the shaft, the respective spirals of the delivery tube being respectively spaced. When spirals of the cryogen delivery tube spin the inflow of cryogen during delivery so as to separate the cryogen into two phases. Also, the spaced spirals of the cryogen delivery tube, the solid core, and an inner surface of the shaft cooperate so as to form a spiraling cryogen exhaust pathway that (i) separates the flow of expanded cryogen flowing from the expansion chamber into two phases, and (ii) urges a heavier liquid phase of the expanded cryogen against a portion of the inner surface of the shaft.

According to still another aspect of the present invention, there is provided a cryosurgical instrument having a hollow shaft having a closed distal end forming a tip, the instrument including a phase separator that includes: a solid core element disposed within the shaft and extending along a longitudinal axis of the shaft; and a coiled cryogen delivery tube that (i) spirals around the longitudinal axis such that the respective spirals are spaced from each other. The respective spirals are in fluid tight contact with the core and an inner surface of the shaft. The spaced spirals of the cryogen delivery tube, the solid core, and an inner surface of the shaft cooperate so as to form a spiraling cryogen exhaust pathway that spins a flow of expanded cryogen flowing away from the tip. The spinning causes separation of the flow of expanded cryogen into a liquid phase and a gaseous phase and urges a heavier liquid phase of the expanded cryogen against a portion of the inner surface of the shaft.

According to still another aspect of the present invention, there is provided a method, including: directing a flow of cryogen to an expansion chamber at a tip end of a shaft of a cryosurgical instrument; permitting cryogen in the expansion chamber to expand and cool at least the tip of the cryosurgical instrument; directing a flow of expanded cryogen into an exhaust pathway so that the flow of expanded cryogen flows away from the tip; and spinning the flow of expanded cryogen. The spinning separates the expanded cryogen into a liquid phase and a gas phase and urges the liquid phase into contact with an inner surface of the shaft.

The aforementioned and/or other features, aspects, details, utilities, and advantages of the present invention are: set forth in the detailed description which follows and/or illustrated in the accompanying drawings; possibly inferable from the detailed description and/or illustrated in the accompanying drawings; and/or learnable by practice of the present invention.

This Summary is provided to introduce a selection of concepts in a simplified form that are further described below in the Detailed Description. This Summary is neither intended to identify key features or essential features of the claimed subject matter, nor should it be used to limit the scope of the claimed subject matter. Furthermore, the claimed subject matter is not limited to implementations that solve any disadvantage noted in any part of this application.

BRIEF DESCRIPTION OF THE DRAWINGS

The present invention will be more readily understood from the detailed description of embodiments thereof made in conjunction with the accompanying drawings of which.

DETAILED DESCRIPTION

Figure 1A:
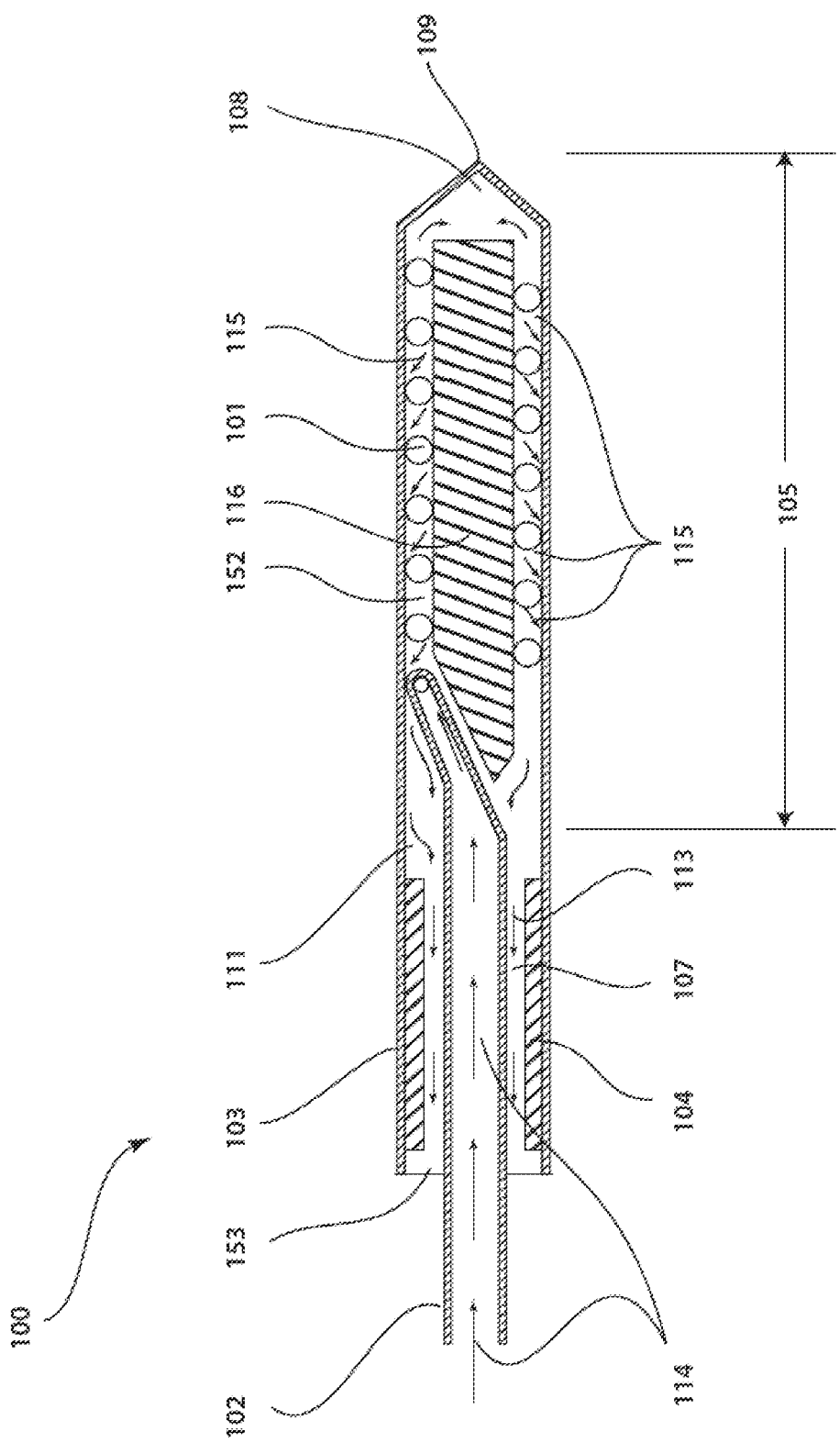
FIG. 1A is cross-sectional view of a non-limiting example of a cryosurgical instrument consistent with an exemplary embodiment of the present invention.

Reference will now be made in detail to embodiment(s) of the present invention, examples of which is/are illustrated in the accompanying drawings, wherein like reference numerals refer to the like elements throughout. The embodiment(s) is/are described below to explain the present invention by referring to the figures.

Although the following text sets forth a detailed description of at least one embodiment or implementation, it is to be understood that the legal scope of protection of this application is defined by the words of the claims set forth at the end of this disclosure. The detailed description is to be construed as exemplary only and does not describe every possible embodiment since describing every possible embodiment would be impractical, if not impossible. Numerous alternative embodiments and/or implementations are both contemplated and possible, using either current technology or technology developed after the filing date of this patent, which would still fall within the scope of the claims.

It is to be understood that, unless a term is expressly defined in this application using the sentence "As used herein, the term "is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term is limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

As used herein, the term centrifugal force refers to the tendency of a flow following a curved path to be urged away from the center of curvature due to inertia. Centrifugal force is referred to as a force for convenience and ease of explanation. This centrifugal force urges the liquid phase of two-phase flow following a curved path to be urged away from the center of curvature due to greater specific gravity than the gaseous phase.

Figure 1B:
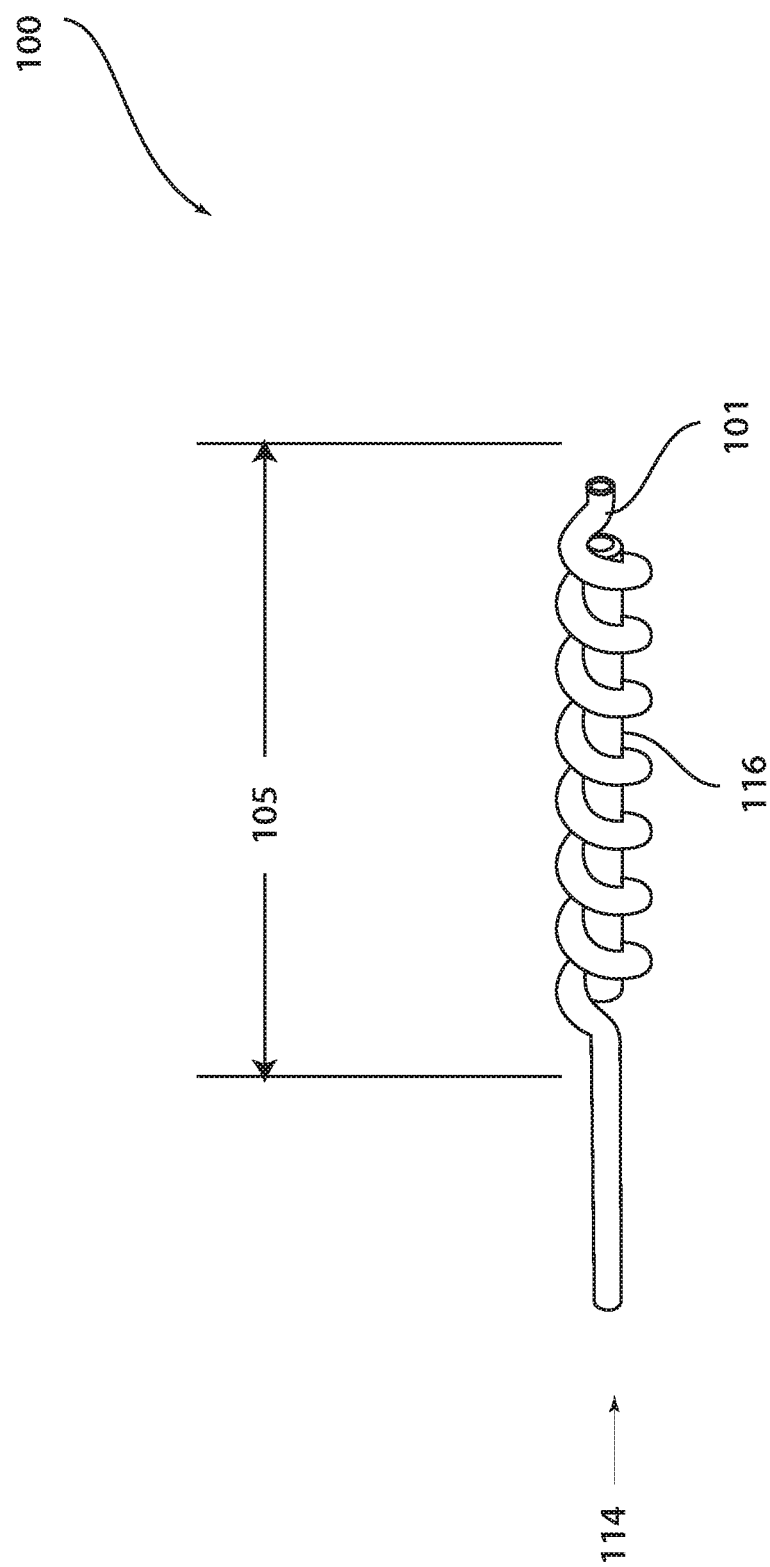
FIG. 1B is a perspective view of portions of heat exchanging components of the cryosurgical instrument of FIG. 1A.

Referring to FIGS. 1A and 1B, there is shown a non-limiting example of a cryosurgical instrument comprising a heat exchanger that features multiple helical coils, which is consistent with an exemplary embodiment of the present invention.

As shown, the cryosurgical instrument 100 includes a shaft 103 surrounding an inlet 102, a core 116, a coiled (i.e. helical) cryogen delivery tube 101, and a tip 109. A rear portion of the instrument 100 includes insulation 104 that separates the inner surface of the shaft 103 from a return flow 113 of cryogen.

The portion of the cryosurgical instrument from the tip 109 to the insulation 104 defines a cooling zone 105. This cooling zone is where heat is exchanged between the cryogen and the cryoprobe. Thus, the freezing (ablation) of tissue occurs around the cooling zone 105, when the instrument is in operation and in contact with tissue.

The inlet 102 receives cryogen and delivers the received cryogen into the shaft 103. As explained above, the shaft 103 features insulation 104 that surrounds the shaft 103 and is mounted to the inner surface of the shaft 103. The insulation 104 is disposed outside of the cooling (heat exchange) zone 105. The presence of the insulation 104 ensures that freezing occurs only where treatment is desired, which is generally around the cooling zone 105.

The core 116 is disposed lengthwise along a longitudinal or lengthwise axis of the cryosurgical instrument. For this reason, it is preferable that the core has a substantially cylindrical shape with a substantially circular cross-section. It is to be understood, that the core may have other cross-sectional shapes.

In operation, cryogen enters through the inlet 102, as indicated by arrows 114, and is directed to coil 101. This inflowing of cryogen then enters the coil 101 and flows in the helical coil such that it spirals around the core 116 as it travels toward the tip 109. This spinning of the inflowing cryogen causes the cryogen to at least partially separate into a liquid phase and a gaseous phase, with the heavier liquid phase tending to displace the gaseous phase along the inner surface of the coil 101. The return flow, indicated by arrows 115, flows in the spiral gap created by the outside surface of the coil 101, the inner surface of the shaft 103, and the outer surface of the core 116.

The relationship between the coil 101 and the core 116, and the cooling zone is illustrated in FIG. 1B.

As cryogen exits the coil 101, it is reflected against a reflective surface 108 of the tip 109. In the illustrated embodiment, the tip 109 is hollow, and the reflective surface 108 is optionally placed close to the inner surface of tip 109, as shown. It is to be understood, however, that the tip 109 need not be hollow and/or the reflective surface 108 may be placed distal to the inner surface of the tip 109 (not shown).

The inflowing cryogen (indicated by arrows 114) boils at the inner side of the reflective surface 108 and in a return flow gap 152 between the coiled tubes of the coil 101, the core 116, and the inner surface of the outer shaft 103. This volume defined by the reflective surface 105, the distal end of the core 116 and the return flow gap 152 represents an expansion chamber. The boiling that occurs in the expansion chamber cools the cooling zone 105 as heat energy is absorbed by the expanding cryogen.

The cryogen exhaust flow is discussed.

After being reflected by the reflective surface 108, the exhausted cryogen flows through the gap 152 between the heat exchanger 101 and the shaft 103, as shown. The curved gap 152 enhances the continued boiling of the liquid phase close to the external wall, as described before. The direction of this return flow is shown by return flow arrows 115. The cryosurgical instrument 100 may optionally include a solid core 116 at the innermost part of the shaft 103 and in cooling zone 105, such that neither the coil 101 nor the gap 152 are present within the core 116. Instead, both the coil 101 and the gap 152 are preferably arranged around the core 116 as shown. However, as previously described, heat exchange between the inlet and the outlet flow is negligible in this arrangement, due to the negligible temperature difference between the respective flows.

The return flow of exhausted cryogen leaves the cooling zone 105 and continues as the return flow 113, as shown, through a return plenum 111 and into a return gap 107. The exhausted cryogen then exits through a cryogen exhaust outlet 153 at an end of the cryosurgical instrument 100 distal from the tip 109.

The return flow is preferably permitted only between the inlet tube of the coil 101 and the inner surface of the shaft 103 at the cooling zone 105, by providing a core 116 that prevents the return flow from returning through the inner gap of the cryosurgical instrument 100 (i.e., the inlet and the return flow are centrifugal). Flow in the center of the helical coil (defined by the coils of the coil 1014) would have been straight.

As the foregoing detailed description illustrates, an aspect of the present invention yields a heat exchanger that advantageously uses centrifugal force to separate an exhaust flow of cryogen into two phases by spinning a flow of cryogen. To do so, the exhaust flow is directed away from the expansion chamber in a spiraling manner between the core and the inner surface of the shaft. This spiraling urges the heavier liquid phase of the exhaust cryogen against the inner surface of the shaft, which encourages enhanced cooling in the cooling zone since the liquid phase has a higher heat capacity (i.e. thermal capacity) than the gaseous phase. Additionally, the incoming flow of cryogen, which is delivered via a helical coil, also spins and tends to separate into liquid and gaseous phases.

As the foregoing also illustrates, the spiraling flow of the exhausted cryogen is achieved by the cooperation of a solid core element extending along a longitudinal axis of the heat exchanger and a cryogen delivery tube that spirals around and contacts the solid core element. In particular, the spirals of the cryogen delivery tube are respectively spaced from each other and in fluid tight contact with both (1) the solid core and (2) the inner surface of the shaft, so as to form a spiraling cryogen exhaust pathway from the distal end of the shaft to the proximal end of the shaft.

Still further, it is to be appreciated that the phase separation that occurs may occur during cryogen delivery and/or during cryogen exhaust. It may be partial, substantially complete, or complete. Indeed, it may be partial during delivery and completed during exhaust. Also, it is to be appreciated that the amount of phase separation during delivery may be the same or different than the amount of phase separation during exhaust.

Examples of various features/aspects/components/operations have been provided to facilitate understanding of the disclosed embodiments of the present invention. In addition, various preferences have been discussed to facilitate understanding of the disclosed embodiments of the present invention. It is to be understood that all examples and preferences disclosed herein are intended to be non-limiting.

Although selected embodiments of the present invention have been shown and described individually, it is to be understood that at least aspects of the described embodiments may be combined.

Although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

What is claimed is:

1. A cryosurgical instrument comprising:
   a shaft having a closed distal end defining an expansion chamber and an open proximal end adapted and configured (i) to receive an inflow of cryogen and (ii) to exhaust a flow of expanded cryogen; and
   a heat exchanger comprising:
   a solid core element extending along a longitudinal axis of the heat exchanger; and
   a cryogen delivery tube that spirals around and contacts the solid core element,
   wherein the spirals of the cryogen delivery tube are spaced from each other and in fluid tight contact with the solid core and an inner surface of the shaft so as to form a cryogen exhaust pathway that spirals around the solid core element.

2. The cryosurgical instrument of claim 1, wherein the cryogen delivery tube spirals only in an ablation zone.

3. A cryosurgical instrument comprising:
   a shaft having a closed distal end defining an expansion chamber at which cryogen boils and a proximal end adapted and configured (i) to receive an inflow of cryogen, (ii) deliver the inflow of cryogen to the expansion chamber, and (iii) to exhaust a flow of cryogen that has expanded in the expansion chamber;
   a solid core element extending along a longitudinal axis of the shaft; and a helical cryogen delivery tube that spirals around the core, is in fluid tight contact with the core, and is in fluid tight contact with an inner surface of the shaft, the respective spirals of the delivery tube being respectively spaced, wherein, when spirals of the cryogen delivery tube spin the inflow of cryogen during delivery so as to separate the cryogen into two phases, and wherein the spaced spirals of the cryogen delivery tube, the solid core, and an inner surface of the shaft cooperate so as to form a spiraling cryogen exhaust pathway that (i) separates the flow of expanded cryogen flowing from the expansion chamber into two phases, and (ii) urges a heavier liquid phase of the expanded cryogen against a portion of the inner surface of the shaft.

4. A cryosurgical instrument having a hollow shaft having a closed distal end forming a tip, the instrument comprising:
a phase separator that includes:
a solid core element disposed within the shaft and extending along a longitudinal axis of the shaft; and
a coiled cryogen delivery tube that (i) spirals around the longitudinal axis such that the respective spirals are spaced from each other,
wherein the respective spirals are in fluid tight contact with the core and an inner surface of the shaft,
wherein the spaced spirals of the cryogen delivery tube, the solid core, and an inner surface of the shaft cooperate so as to form a spiraling cryogen exhaust pathway that spins a flow of expanded cryogen flowing away from the tip,
wherein the spinning causes separation of the flow of expanded cryogen into a liquid phase and a gaseous phase; and wherein the spinning urges a heavier liquid phase of the expanded cryogen against a portion of the inner surface of the shaft.

5. A cryosurgical instrument comprising:
a shaft having a closed distal end defining an expansion chamber at which cryogen boils and a proximal end adapted and configured (i) to receive an inflow of cryogen, (ii) deliver a received inflow of cryogen to the expansion chamber, and (iii) to exhaust a flow of cryogen that has expanded in the expansion chamber;
a solid core element extending along a longitudinal axis of the shaft; and
a helical cryogen delivery tube that spirals around the core, is in fluid tight contact with the core, and is in fluid tight contact with an inner surface of the shaft, the respective spirals of the delivery tube being respectively spaced,
wherein, when spirals of the cryogen delivery tube spin the received inflow of cryogen so as to separate the cryogen into two phases, and
wherein the spaced spirals of the cryogen delivery tube, the solid core, and an inner surface of the shaft cooperate so as to form a spiraling cryogen exhaust pathway that separates cryogen flowing therethrough from the expansion chamber into two phases.

6. The cryosurgical instrument of claim 5, wherein the spiraling cryogen exhaust pathway urges a heavier liquid phase of the expanded cryogen against a portion of the inner surface of the shaft.

* * * * *